US012562277B2

(12) United States Patent
Neumann

(10) Patent No.: US 12,562,277 B2
(45) Date of Patent: *Feb. 24, 2026

---

(54) METHOD OF AND SYSTEM FOR DETERMINING A PRIORITIZED INSTRUCTION SET FOR A USER

(71) Applicant: KPN INNOVATIONS, LLC., Lakewood, CO (US)

(72) Inventor: Kenneth Neumann, Lakewood, CO (US)

(73) Assignee: KPN INNOVATIONS LLC, Lakewood, CO (US)

( * ) Notice: Subject to any disclaimer, the term of this patent is extended or adjusted under 35 U.S.C. 154(b) by 78 days.

This patent is subject to a terminal disclaimer.

(21) Appl. No.: 18/233,404

(22) Filed: Aug. 14, 2023

(65) Prior Publication Data

US 2023/0386666 A1 Nov. 30, 2023

Related U.S. Application Data

(63) Continuation-in-part of application No. 16/939,230, filed on Jul. 27, 2020, now Pat. No. 11,756,663.

(51) Int. Cl.
G16H 50/20 (2018.01)
G06N 20/20 (2019.01)
(Continued)

(52) U.S. Cl.
CPC ............. G16H 50/20 (2018.01); G06N 20/20 (2019.01); G16H 20/30 (2018.01); G16H 20/60 (2018.01)

(58) Field of Classification Search
CPC ........ G16H 50/20; G16H 20/30; G16H 20/60; G06N 20/20
See application file for complete search history.

(56) References Cited

U.S. PATENT DOCUMENTS 8,200,548 B2 6/2012 Wiedl
9,805,163 B1 10/2017 Panch et al.
(Continued)

FOREIGN PATENT DOCUMENTS

CN 116195002 A * 5/2023 .......... A61B 5/0006
EP 3272280 A1 1/2018
(Continued)

OTHER PUBLICATIONS

Chatterjee et al., "Machine learning and ontology in eCoaching for personalized activity level monitoring and recommendation generation," Scientific Reports | (2022) 12:19825 | https://doi.org/10.1038/s41598-022-24118-4. (Year: 2022).*
(Continued)

*Primary Examiner* — Jonathon A. Szumny
(74) *Attorney, Agent, or Firm* — Caldwell Intellectual Property Law

(57) ABSTRACT

A system for determining a prioritized instruction set for a user, the system comprising a computing device, wherein the computing device is configured to receive at least a physiological goal and provide a plurality of biological extraction data. Computing device may determine a user baseline profile using training data, wherein training data correlates biological extraction data and physiological goals to baseline profile elements, train a machine-learning model using the training data, and determine the user baseline profile as a function of the machine-learning model. Computing device may generate a differential action as a function of the user baseline profile and the physiological goal, receive a plurality of user preference data, and selecting the differential action from the plurality of candidate differential actions. Computing device may receive an updated biological extraction datum corresponding to the user and may modify the
(Continued)

differential action as a function of the updated biological extraction datum.

20 Claims, 10 Drawing Sheets

(51) Int. Cl.
G16H 20/30 (2018.01)
G16H 20/60 (2018.01)

(56) References Cited

U.S. PATENT DOCUMENTS

| | | | |
|---|---|---|---|
| 10,026,055 B2 | 7/2018 | Riel-Dalpe et al. | |
| 10,130,311 B1 | 11/2018 | De Sapio et al. | |
| 11,094,016 B1 | 8/2021 | Welz et al. | |
| 2002/0004749 A1 | 1/2002 | Froseth et al. | |
| 2004/0210621 A1 | 10/2004 | Antonellis | |
| 2010/0280895 A1 | 11/2010 | Mottola | |
| 2011/0046972 A1* | 2/2011 | Leverette | G16H 50/30 |
| | | | 705/2 |
| 2011/0093249 A1 | 4/2011 | Holmes et al. | |
| 2014/0058794 A1 | 2/2014 | Malov et al. | |
| 2014/0255882 A1 | 9/2014 | Hadad et al. | |
| 2015/0150074 A1* | 5/2015 | Nolan | H04L 63/10 |
| | | | 726/1 |
| 2015/0227888 A1 | 8/2015 | Levanon et al. | |
| 2016/0372005 A1 | 12/2016 | Bajpai et al. | |
| 2017/0024789 A1 | 1/2017 | Frehn et al. | |
| 2017/0372197 A1 | 12/2017 | Baughman et al. | |
| 2018/0060494 A1 | 3/2018 | Dias et al. | |
| 2018/0075219 A1 | 3/2018 | Klein et al. | |
| 2018/0293638 A1 | 10/2018 | Simpson | |
| 2018/0308066 A1 | 10/2018 | Hadatsuki | |
| 2019/0043143 A1 | 2/2019 | Camacho et al. | |
| 2019/0065687 A1 | 2/2019 | Mei et al. | |
| 2019/0198149 A1 | 6/2019 | Bastide et al. | |
| 2019/0317998 A1 | 10/2019 | Komine et al. | |
| 2019/0336824 A1 | 11/2019 | Fung | |
| 2019/0355454 A1 | 11/2019 | Deshpande et al. | |
| 2020/0065892 A1 | 2/2020 | Brown | |
| 2020/0098466 A1* | 3/2020 | Murdoch | G16H 20/60 |
| 2020/0170549 A1 | 6/2020 | Baykaner et al. | |
| 2020/0250508 A1 | 8/2020 | De Magalhaes et al. | |
| 2020/0367807 A1* | 11/2020 | Lassoued | A61B 5/7275 |
| 2021/0098099 A1* | 4/2021 | Neumann | G06N 20/00 |
| 2021/0153787 A1* | 5/2021 | Parker | A61B 5/6801 |
| 2021/0202067 A1* | 7/2021 | Williams | G06Q 50/265 |
| 2021/0406025 A1 | 12/2021 | Neumann | |
| 2024/0203603 A1* | 6/2024 | Yang | G16H 40/67 |

FOREIGN PATENT DOCUMENTS

| | | | |
|---|---|---|---|
| WO | WO2005013174 A2 | 2/2005 | |
| WO | WO-2016065463 A1 * | 5/2016 | |
| WO | WO-2023012758 A1 * | 2/2023 | A61B 5/165 |
| WO | WO-2024055931 A1 * | 3/2024 | |

OTHER PUBLICATIONS

Liao et al; "Multi-Objective Green Meal Delivery Routing Problem Based on a Two-Stage Solution Strategy", Journal of Cleaner Production, vol. 258, Jun. 10, 2020, 120627 https://www.sciencedirect.com/science/article/pii/S0959652620306740.

Reyes, Damian et al; "The Meal Delivery Routing Problem", H. Milton Stewart School of Industrial Engineering, Georgia Institute of Technology, Atlanta GA 30332-0205; Mar. 1, 2018, Decision Engineering Department, Grubhub, Chicago IL 60602; https://www.semanticscholar.org/paper/The-Meal-Delivery-Routing-Problem-Reyes-Erera/1c0b0f117437f4123cdeb77c24210610733de706.

\* cited by examiner

500

User Baseline Profile 124

116

132

METHOD OF AND SYSTEM FOR DETERMINING A PRIORITIZED INSTRUCTION SET FOR A USER

CROSS-REFERENCE TO RELATED APPLICATIONS

This application is a continuation-in-part of Non-provisional application Ser. No. 16/939,230, filed on Jul. 27, 2020 and entitled "METHOD OF AND SYSTEM FOR DETERMINING A PRIORITIZED INSTRUCTION SET FOR A USER," the entirety of which is incorporated herein by reference.

FIELD OF THE INVENTION

The present invention generally relates to the field of solution optimization. In particular, the present invention is directed to determining a prioritized instruction set for a user.

BACKGROUND

Machine-learning methods are increasingly valuable for analysis of patterns in large quantities of data. However, where the data is large and varied enough, determining a prioritized instruction set for users from machine-learning outputs can become untenable, especially with tradeoffs between sophistication and efficiency.

SUMMARY OF THE DISCLOSURE

In an aspect, a system for determining a prioritized instruction set for a user, the system including a computing device, wherein the computing device is designed and configured to receive, from a user, at least a physiological goal; provide a plurality of biological extraction data corresponding to the user; determine a user baseline profile, wherein determining the user baseline profile further includes receiving training data, wherein the training data includes input data and output data, wherein the input data includes biological extraction data elements and physiological goals data elements, and the output data includes user baseline profile data elements; categorizing the training data as a function of a natural language machine learning process, wherein categorizing the training data includes detecting at least one correlation of the biological extraction data elements and the physiological goals data elements with the baseline profile data elements; training a machine-learning model as a function of the categorized training data; and determining, using the trained machine-learning model, the user baseline profile as a function of the plurality of biological extraction data and the at least a physiological goal; determine a negative tendency of the user based on the baseline profile; generate a differential action as a function of the user baseline profile, the negative tendency, and the at least a physiological goal, wherein generating the differential action further includes generating a plurality of candidate differential actions as a function of the user baseline profile and the physiological goal; receiving a plurality of user preference data; and selecting the differential action from the plurality of candidate differential actions as a function of the user preference data and the at least a physiological goal, wherein selecting the differential action includes creating an objective function; and optimizing a selection procedure of the objective function as a function of the user preference data, the at least a physiological goal, the negative tendency, and the user baseline profile; receive an updated biological extraction datum corresponding to the user; and modify the differential action as a function of the updated biological extraction datum.

In another aspect, a method for determining a prioritized instruction set for a user, the method including a receiving from a user, by computing device, at least a physiological goal; providing, by the computing device, a plurality of biological extraction data corresponding to the user; determining, by the computing device, a user baseline profile, wherein determining the user baseline profile further includes receiving training data, wherein the training data includes input data and output data, wherein the input data includes biological extraction data elements and physiological goals data elements, and the output data includes user baseline profile data elements; categorizing the training data as a function of a natural language machine learning process, wherein categorizing the training data includes detecting at least one correlation of the biological extraction data elements and the physiological goals data elements with the baseline profile data elements; training a machine-learning model as a function of the categorized training data; and determining, using the trained machine-learning model, the user baseline profile as a function of the plurality of biological extraction data and the at least a physiological goal; determining, by the computing device, a negative tendency of the user based on the baseline profile; generating, by the computing device, a differential action as a function of the user baseline profile, the negative tendency, and the at least a physiological goal, wherein generating the differential action further includes generating a plurality of candidate differential actions as a function of the user baseline profile and the physiological goal; receiving a plurality of user preference data; and selecting the differential action from the plurality of candidate differential actions as a function of the user preference data and the at least a physiological goal, wherein selecting the differential action includes creating an objective function; and optimizing a selection procedure of the objective function as a function of the user preference data, the at least a physiological goal, the negative tendency, and the user baseline profile; receiving, by the computing device, an updated biological extraction datum corresponding to the user; and modifying, by the computing device, the differential action as a function of the updated biological extraction datum.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for determining a prioritized instruction set for a user. In an embodiment, a system may include a computing device, wherein the computing device is designed and configured to receive, from a user, at least a physiological goal, and provide a plurality of biological extraction data corresponding to the user. Computing device may determine a user baseline profile, wherein determining the user baseline profile further comprises receiving training data including data entries, each data entry correlating biological extraction data and physiological goals to baseline profile elements, training a machine-learning model as a function of the training data; and determining the user baseline profile as a function of the machine-learning model, the plurality of biological extraction data and the at least a physiological goal. Computing device may generate a differential action as a function of the user baseline profile and the at least a physiological goal, wherein generating the differential action further comprises generating a plurality of candidate differential actions as a function of the user baseline profile and the physiological goal, receiving a plurality of user preference data; and selecting the differential action from the plurality of candidate differential actions as a function of the user preference data and the at least a physiological goal. Computing device may receive an updated biological extraction datum corresponding to the user. Computing device may modify the differential action as a function of the updated biological extraction datum.

Figure 1:
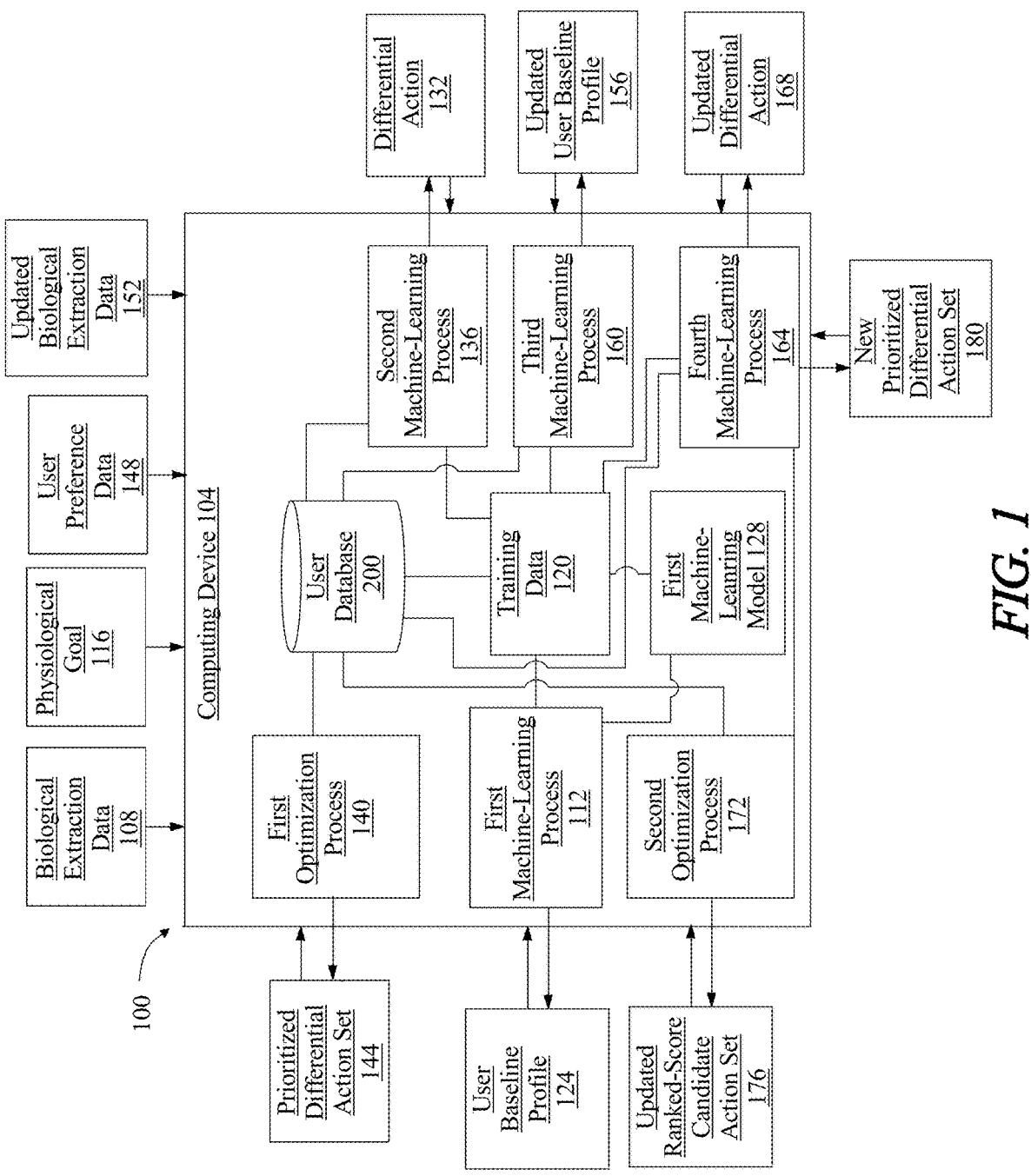
FIG. 1 is a block diagram illustrating an exemplary embodiment of a system for determining a prioritized instruction set for a user.

Referring now to FIG. 1, an exemplary embodiment of a system 100 for determining a prioritized instruction set for a user is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Continuing to refer to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With further reference to FIG. 1, computing device is designed and configured to receive, from a user, at least a physiological goal. A "physiological goal," as used in this disclosure, is a desired change in a physiological state of a user, as it relates to a user baseline profile, as described in further detail below. Computing device 104 may be configured to determine physiological state of a user as a function of a biological extraction as described in further detail below. Biological extraction data 108 as used herein may include, for instance, data used as a biological extraction as described in U.S. Nonprovisional application Ser. No. 16/502,835, filed on Jul. 3, 2019, and entitled "METHODS AND SYSTEMS FOR ACHIEVING VIBRANT CONSTITUTION BASED ON USER INPUTS," the entirety of which is incorporated herein by reference.

Figure 2:
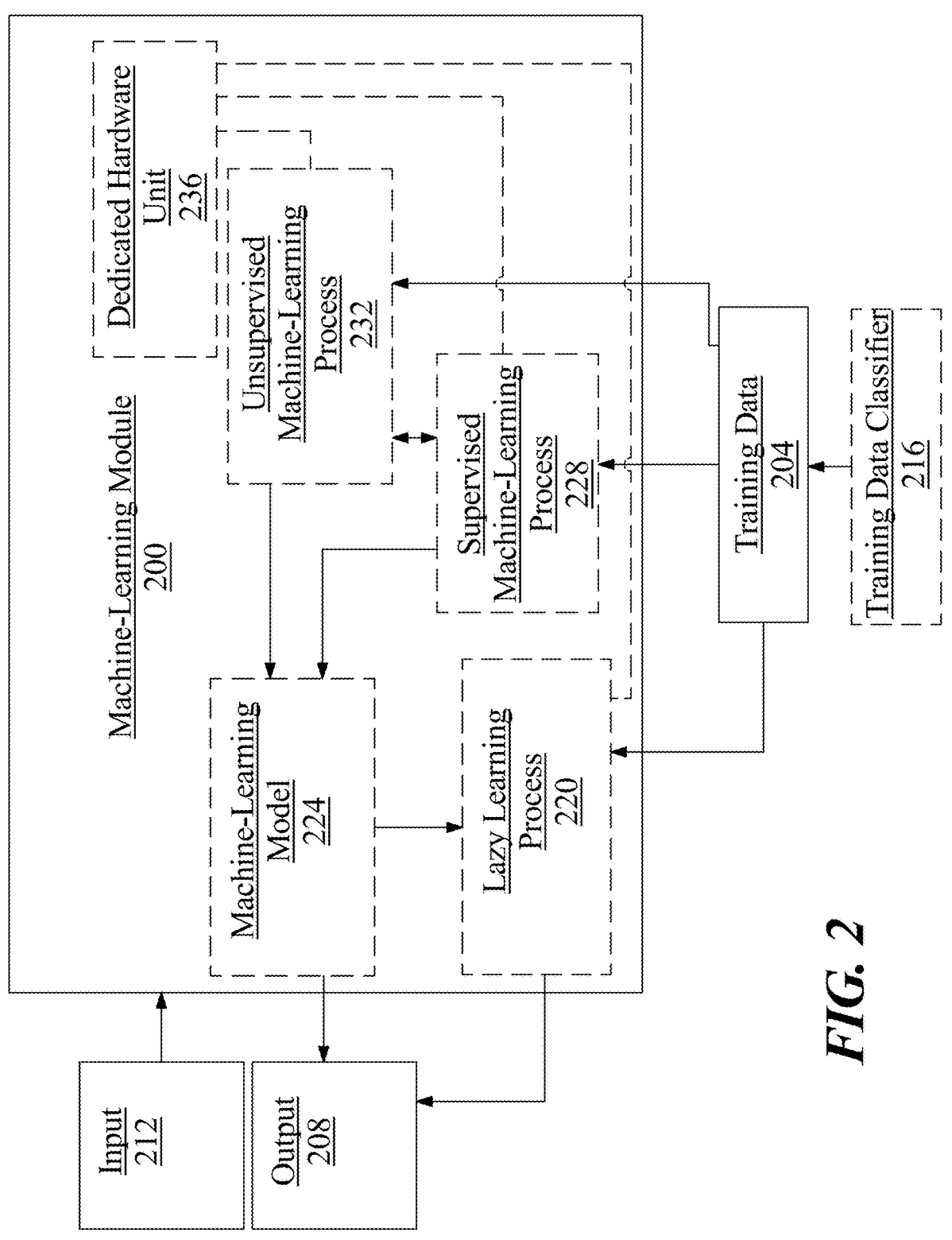
FIG. 2 is a block diagram illustrating an exemplary embodiment of a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example, biological extraction data as an input and a user baseline as an output.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to user baseline profile datum of a cohort of users sharing similar positive, neutral, and/or negative tendencies as described further below. Supervised machine-learning processes may include, without limitation, machine-learning processes as described in U.S. Nonprovisional application Ser. No. 16/520,835, filed on Jul. 3, 2019, and entitled "METHODS AND SYSTEMS FOR ACHIEVING VIBRANT CONSTITUTION BASED ON USER INPUTS," the entirety of which is incorporated herein by reference.

Still referring to FIG. 2, he use a of a machine-learning process/model as described herein may improve the functioning of computing device 104 in performing processes that collectively generate a prioritized instruction set for a user. For example, a machine-learning model, such as first machine-learning model 128, improves the performance power of computing device 104 by generating the at least a user baseline profile 124, wherein user baseline profile 124 includes a summation of user biological extraction data 108, including any relationships between elements of data, including any mathematical, causative, correlational relationships, or the like, between elements of data as it pertains to a user's baseline health, including current diseases, potential risks, diagnoses, addictions, proclivities, tendencies, or the like as described further below. The quantity of data that goes into generating user baseline profile 124 may vary and fluctuate based on a plurality of variables, such as the quantity and type of biological and physiological data received from a user. Without the implementation of a machine-learning model, there would be a trade in the performance power of computing device 104, such as time and accuracy, in order to determine the relationships between the elements of data that is then used in other processing step, as described further below to, as described further below, in order to a determine a prioritized instruction set for a user. The ability to continuously train a machine-learning model cable of learning to identify new trends or correlations within a fluctuating quantity of data is a benefit that would not be realized otherwise, without the tradeoff in performance efficiency. In some embodiments, the performance of the machine-learning model may be assed based on user feedback received from a computing device, database, or user interface as described through this disclosure. "User feedback," as used herein, is information, opinions, and comments provided by a user regarding an output of system 100. For example, user feedback may contain information describing the inaccuracy along with a replacement correlation between biological and physiological data as described above to a user baseline. Training data as described herein may be updated to implement or correspond to user feedback as received.

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may downsample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Antialiasing and/or anti-imaging filters, and/or low-pass filters, may be used to clean up side-effects of compression.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs as described in this disclosure as inputs, outputs as described in this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

In reference to FIG. 1, computing device 104 may be configured to determine a user baseline profile 124 training first machine-learning process 112 as a function of the training data 120. Training data 120 may refer to at least an element of biological extraction data 108. Training data 120 may correspond to a subset of data, classified using a classification process for training a first machine-learning process 112. Training data 120 may be generated using a classifier generated by a classification process, as described above.

Still referring to FIG. 1, a machine-learning module 200 using a first training set 208 may refer to using a first machine-learning process 112 trained with training data 120 to generate a first machine-learning model 128. A first machine-learning model 128 may be used with a first machine-learning process 112 for generating the at least a user baseline profile 124, wherein a first machine-learning process 122 may accept an input of user biological extraction data 108 and an input of at least an element of data retrieved from a database, and a first machine-learning model 128 to generate a user baseline profile 124 as an output. In non-limiting illustrative examples, a first machine-learning model 112 may represent a mathematical model describing the tractability of a physiological goal of 'lowering blood pressure,' as a function of user biological extraction data 108 as it pertains to the user's current blood pressure, including diet, genetics, lifestyle, demographic, fitness, and the like. In further non-limiting illustrative examples, such a first machine-learning model 128 may be used by a first machine-learning process 112 with an input of user biological extraction data 108, and a function, numerical value, matrix, vector, heuristic, or similar quantitative and/or qualitative relationship correlating biological extraction data to a user baseline profile, retrieved from an online repository, published research, database, or the like, to output a user baseline profile. A "user baseline profile," as described in this disclosure refers to a graphical output of a summation of user biological extraction data 108, including any relationships between elements of data, including any mathematical, causative, correlational relationships, or the like, between elements of data as it pertains to a user's baseline health, including current diseases, potential risks, diagnoses, addictions, proclivities, tendencies, or the like. In non-limiting illustrative examples, a user baseline profile 124 may capture all mathematical relationships between a user's baseline health, the provided biological extraction data 108, an at least a physiological goal. In further non-limiting illustrative examples, a user baseline profile may describe a pattern of sleep behavior of a user related to level of exercise and/or fitness of a user to model a user's tendency for overtraining as a potential obstacle in achieving a physiological goal, and how overtraining may manifest is other user biological extraction data 108, for instance with blood pressure, visceral fat, irritability, etc. A user baseline profile 124 and/or any machine-learning models, classifiers, subsets of data, including biological user data 108, other user baseline profiles 124, machine-learning processes, and the like may be stored and/or retrieved from a database, as described in further detail below.

Figure 3:
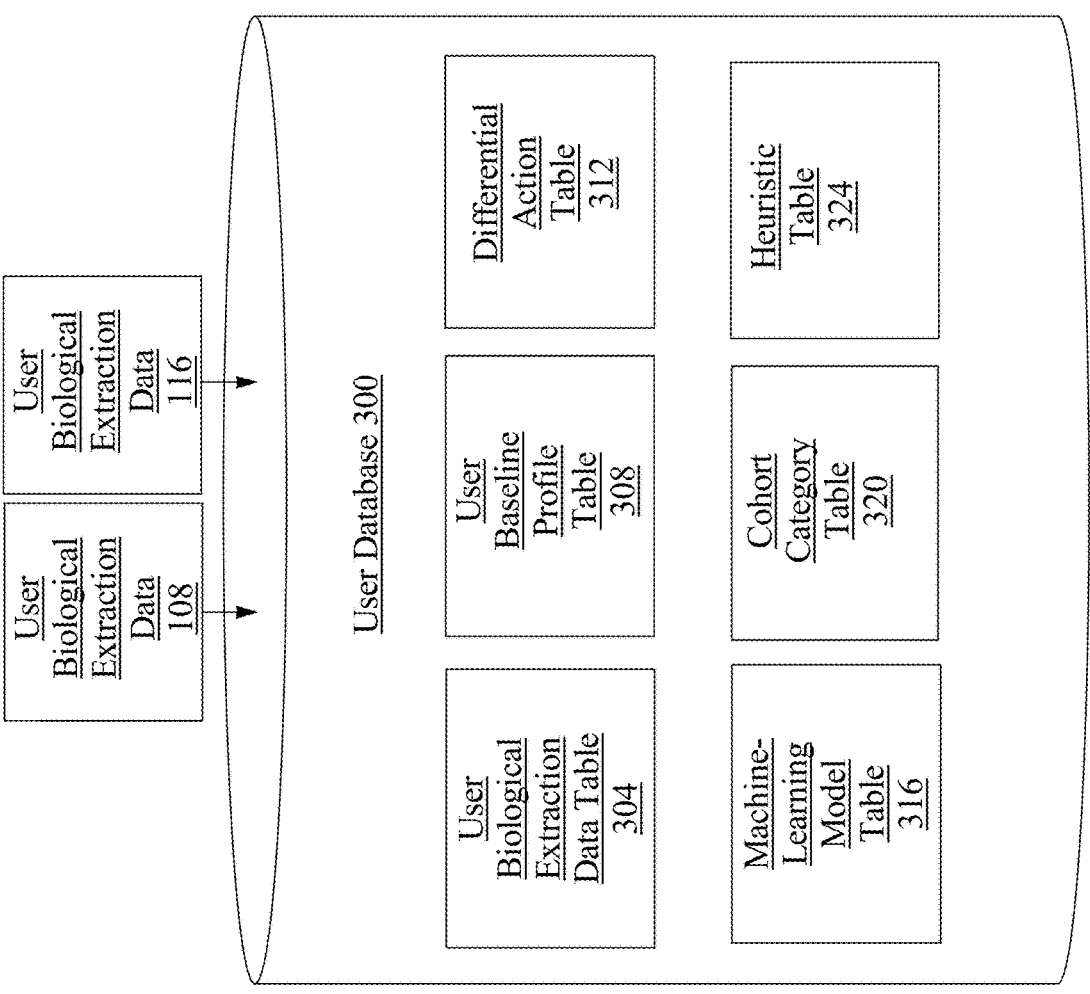
FIG. 3 is a block diagram illustrating an exemplary embodiment of a user database.

Referring now to FIG. 3, a non-limiting exemplary embodiment of a user database 300 is illustrated. Database may refer to a "user database" which at least a computing device 104 may, alternatively or additionally, store and/or retrieve data from a user biological extraction table 304, user baseline profile table 308, differential action table 312, machine-learning model table 316, cohort category table 320, and/or heuristic table 324. Determinations by a machine-learning process may also be stored and/or retrieved from the user database 120, for instance in non-limiting examples a classifier describing a subset of data, a machine-learning model that was trained using training data, and/or training data. As a non-limiting example, user database 120 may organize data according to one or more instruction tables. One or more user database 120 tables may be linked to one another by, for instance in a non-limiting example, common column values. For instance, a common column between two tables of user database 300 may include an identifier of a submission, such as a form entry, textual submission, research paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which data from one or more tables may be linked and/or related to data in one or more other tables.

Still referring to FIG. 3, in a non-limiting embodiment, one or more tables of a user database 300 may include, as a non-limiting example, a user biological extraction data table 304, which may include biological extraction analyses for use in predicting goals of a user and/or differential actions for a user and/or correlating user data to other users, entries indicating degrees of relevance to and/or efficacy in predicting a goal of a user, and/or other elements of data computing device 104 and/or system 100 may use to determine usefulness and/or relevance of user data in determining goals, instructions, and/or changes in goals and/or instructions as described in this disclosure. One or more tables may include a user baseline table 308, which may correlate user data, goals, outcomes, models, heuristics, and/or combinations thereof to one or more measures of a in achieving a goal, and/or relationships to a physiological goal. One or more tables may include, without limitation, a differential action table 312 which may contain one or more inputs identifying one or more categories of data, for instance numerical values describing the propensity of a user to follow a differential action, or the long-term effect a differential action has on future physiological goals. One or more tables may include, without limitation, a machine-learning model table 316 which may contain one or more models generated from a machine-learning process and training data. One or more tables may include, without limitation, a cohort category table 320 which may contain one or more inputs identifying one or more categories of data, for instance demographic data, physiological data, sleep pattern data, spending data, or the like, with regard to which users having matching or similar data may be expected to have similar goals and/or instruction sets as a result of optimization program output elements and/or other user data input elements. One or more tables may include, without limitation, a heuristic table 324 which may include one or more inputs describing potential mathematical relationships between at least an element of user data and goals, instructions, and rankings thereof, change in goals and/or instructions over time, and/or scoring functions for determining a rank-ordered set of goals and/or instructions, as described in further detail below.

Continuing in reference to FIG. 1, computing device 104 may generate a plurality of differential actions 132 using a second machine-learning 136 process to calculate a difference between a physiological goal 116 and a user baseline profile 124, and may retrieve from a database, a candidate differential action 132 to address a difference between a physiological goal 116 and a user baseline profile 124. A "differential action," as described in this disclosure refers to any action prescribed to a user to work towards achieving a physiological goal 116. Generating a differential action 132 may include using a second machine-learning process 136 to calculate a difference between an element of a physiological goal 116 and an element of a user baseline 124. A second machine-learning process 136 may refer to a machine-learning module 200, as described above. In non-limiting illustrative examples, a second machine-learning process 136 may include using a training set 208 including training data 120, wherein training data 120 may be data corresponding to a user baseline profile 124, a physiological goal 116, a plurality of differential actions 132, and the like. In further non-limiting illustrative examples, a second machine-learning process 136 may use training data 120 that is identified by a classifier, and/or may refer to a data that corresponds to a second user. A second machine-learning process 136 may accept an input of at least a physiological goal 116 and a user baseline 124 to generate at least a differential action 132, of a plurality of candidate differential actions. A second machine-learning process 136 may generate a differential action 132 by retrieving an element of data from a user database 200 as it correlates to achieving a physiological goal 116 as a function of the user baseline profile 124; for instance and without limitation, this may be a query for options in addressing a physiological goal 116, with a mathematical function, matrix, vector, numerical value, or the like, that applies the user baseline profile 124 to the retrieved options. For instance in non-limiting examples, a second machine-learning process 136 may query a database for a plurality of candidate differential actions 132 in addressing a physiologic goal 116 of 'reducing blood pressure into a healthy range,' wherein candidate differential actions 132 retrieved from a database may depend on current user blood pressure, and the healthy range is for a particular user. In further non-limiting illustrative examples, a second machine-learning process 136 may use a mathematical function to compare the current user blood pressure, among other factors, to the queried 'healthy blood pressure range' according to the user baseline profile 124 to determine the efficacy of candidate differential actions 132, for instance a therapeutic dose of a blood pressure medicine, a new diet, lowering caffeine, sodium, and/or alcohol intake, and/or meditation techniques.

Figure 4:
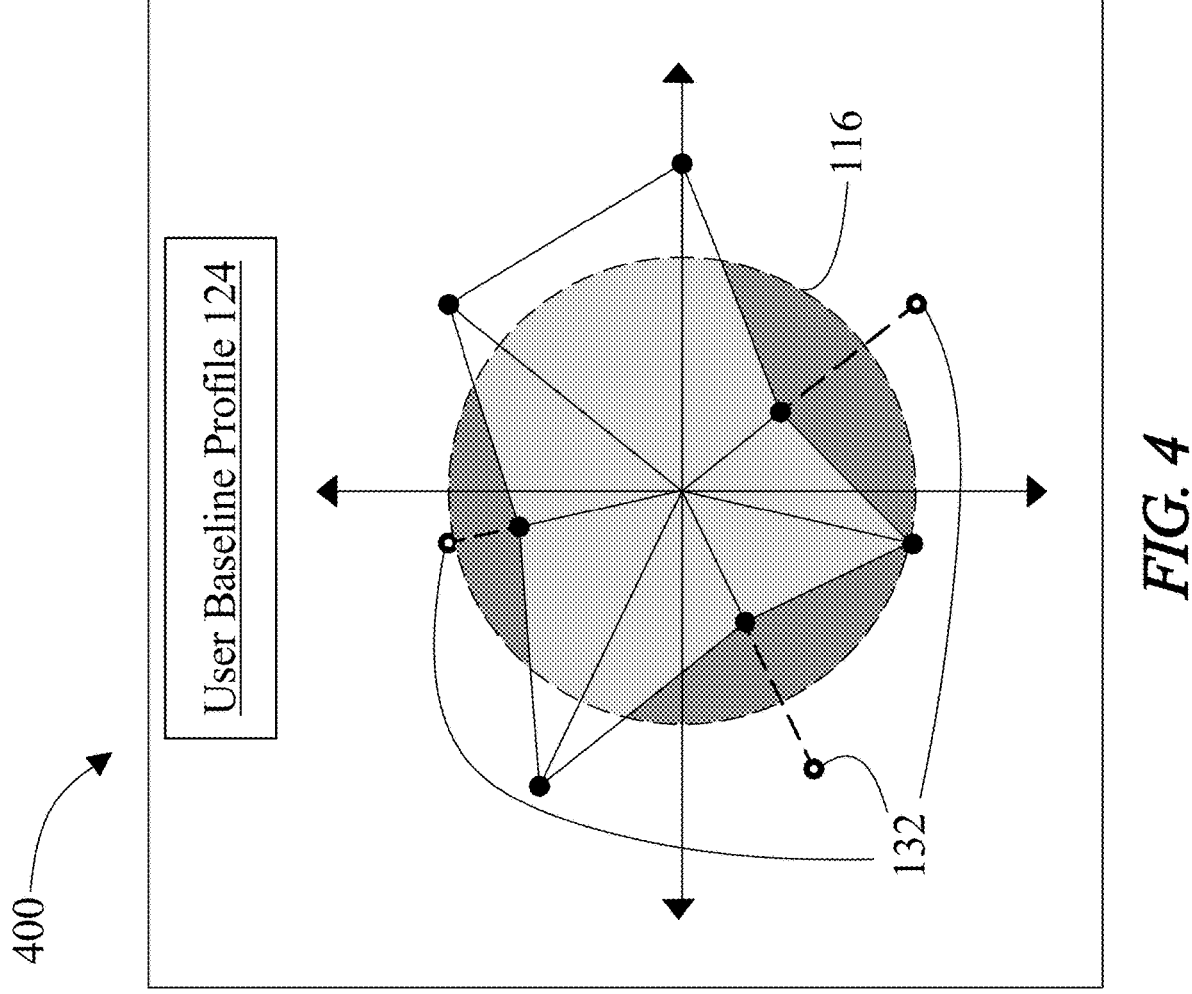
FIG. 4 is a diagrammatic representation of a user baseline profile as a function of the plurality of biological extraction data.

Referring now to FIG. 4, a diagrammatic representation of a user baseline profile 124 as a function of the plurality of biological extraction data 400 is illustrated. In non-limiting illustrative embodiments, a user baseline profile 124 may be illustrated as a series of points, representing polar coordinates, radial vectors, or the like, that correspond to a measure of an element of a plurality of elements that may be included a user baseline profile 124. Elements included in a user baseline profile 124 may be a variety of physiological data regarding, for instance without limitation, sleep duration, frequency, and/or quality; physical fitness, strength, endurance, and/or cardiovascular shape; medical history data including major hospitalizations, diagnoses, surgeries, current medications, BMI, and/or age; blood chemistry data, among other data, as described above. In non-limiting illustrative embodiments, the areas between points, illustrated as the lighter grey shaded spaces, denote the overall user baseline profile 124 as it pertains to having satisfied, achieved, reached, or otherwise addressed elements corresponding to a physiological goal 116, denoted by the black dotted-line circle. In non-limiting illustrative embodiments, the area under the black dotted-line circle, illustrated as the darker grey shaded area, may correspond to regions of the user baseline profile 124 that do not meet a physiological goal 116. In non-limiting illustrative embodiments, differential actions 132 denoted as black radial, dashed-lines and empty circles, may then be determined by a machine-learning process to address deficiencies in a user baseline profile 124 in achieving a goal; the distance of each black radial, dashed-lines to an empty circles may correspond to calculated values, functions, vectors, and the like that contain measured data as to the magnitude, degree, timing, and/or impact that each differential action may have in changing the user baseline profile 124 towards achieving a physiological goal 116.

Continuing in reference to FIG. 1, computing device 104 may be configured to generate plurality of candidate differential actions 132 by generating a ranked-score list of candidate differential actions 132 as a function of a physiological goal 116 and a user baseline profile 124. Generating a ranked-score list may include weighting a plurality of candidate actions as a function of a physiological goal 116 and a user baseline profile 124, and then ranking accordingly. Computing device 104 may weight candidate differential actions 132 using a first optimization process 140, as described in further detail below. Weighting differential actions 132 may be performed based upon a scoring function, or the like, using a first optimization process 140. An "optimization process," as described herein refers to optimization performed by one or more 'objective function' used by a computing device 104 to place elements in an optimal listing based upon a score or numerical value, as described in further detail below. A computing device 104 may compute a score associated with each candidate action and select actions to minimize and/or maximize the score, depending on whether an optimal result is represented, respectively, by a minimal and/or maximal score; a mathematical function, described herein as an "objective function," may be used by computing device 104 to score each possible pairing. Objective function may be based on one or more objectives, as described below. Computing device 104 may pair a predicted route, with a given courier, that optimizes objective function. In various embodiments a score of a particular goal may be based on a combination of one or more factors, including user data 116. Each factor may be assigned a score based on predetermined variables. In some embodiments, the assigned scores may be weighted or unweighted, for instance and without limitation as described in the U.S. Nonprovisional application Ser. No. 16/890,686, filed on Jun. 2, 2020, and entitled "ARTIFICIAL INTELLIGENCE METHODS AND SYSTEMS FOR CONSTITUTIONAL ANALYSIS USING OBJECTIVE FUNCTIONS," the entirety of which is incorporated herein by reference.

Optimization of an objective function may include performing a greedy algorithm process. A "greedy algorithm" is defined as an algorithm that selects locally optimal choices, which may or may not generate a globally optimal solution. For instance, computing device 104 may select goals so that scores associated therewith are the best score for each goal. For instance, in non-limiting illustrative example, optimization may determine the combination of routes for a courier such that each delivery pairing includes the highest score possible, and thus the most optimal delivery.

Still referring to FIG. 1, objective function may be formulated as a linear objective function, which computing device 104 may solve using a linear program such as without limitation a mixed-integer program. A "linear program," as used in this disclosure, is a program that optimizes a linear objective function, given at least a constraint. For instance, in non-limiting illustrative examples, a given constraint might be a nutritional deficiency of a user, and a linear program may use a linear objective function to calculate minimized caloric intake for weight loss without exacerbating a nutritional deficiency. In various embodiments, system 100 may determine a set of instructions towards achieving a user's goal that maximizes a total score subject to a constraint that there are other competing goals. A mathematical solver may be implemented to solve for the set of instructions that maximizes scores; mathematical solver may be implemented on computing device 104 and/or another device in system 100, and/or may be implemented on third-party solver.

With continued reference to FIG. 1, optimizing objective function may include minimizing a loss function, where a "loss function" is an expression an output of which an optimization process minimizes to generate an optimal result. As a non-limiting example, computing device 104 may assign variables relating to a set of parameters, which may correspond to score components as described above, calculate an output of mathematical expression using the variables, and select a goal that produces an output having the lowest size, according to a given definition of "size," of the set of outputs representing each of plurality of candidate ingredient combinations; size may, for instance, included absolute value, numerical size, or the like. Selection of different loss functions may result in identification of different potential pairings as generating minimal outputs Weighting a ranked-score list of candidate actions as a function of a physiological goal 116 and a user baseline profile 124 may include using a scoring function to calculate weighting of candidate actions. A scoring function may be stored in and/or retrieved from a user database 300. A scoring function may be used to weight candidate actions on a variety of factors, including without limitation, anticipated versus experienced level of difficulty in executing differential action, tractability of physiological goal, user baseline profile 124 values, severity of physiological issues, among other factors. Weighting of differential actions 132 based on at least a factor may then provide numerical data for generating a ranked-score list to place candidate actions in a logical order based on weights.

Figure 5:
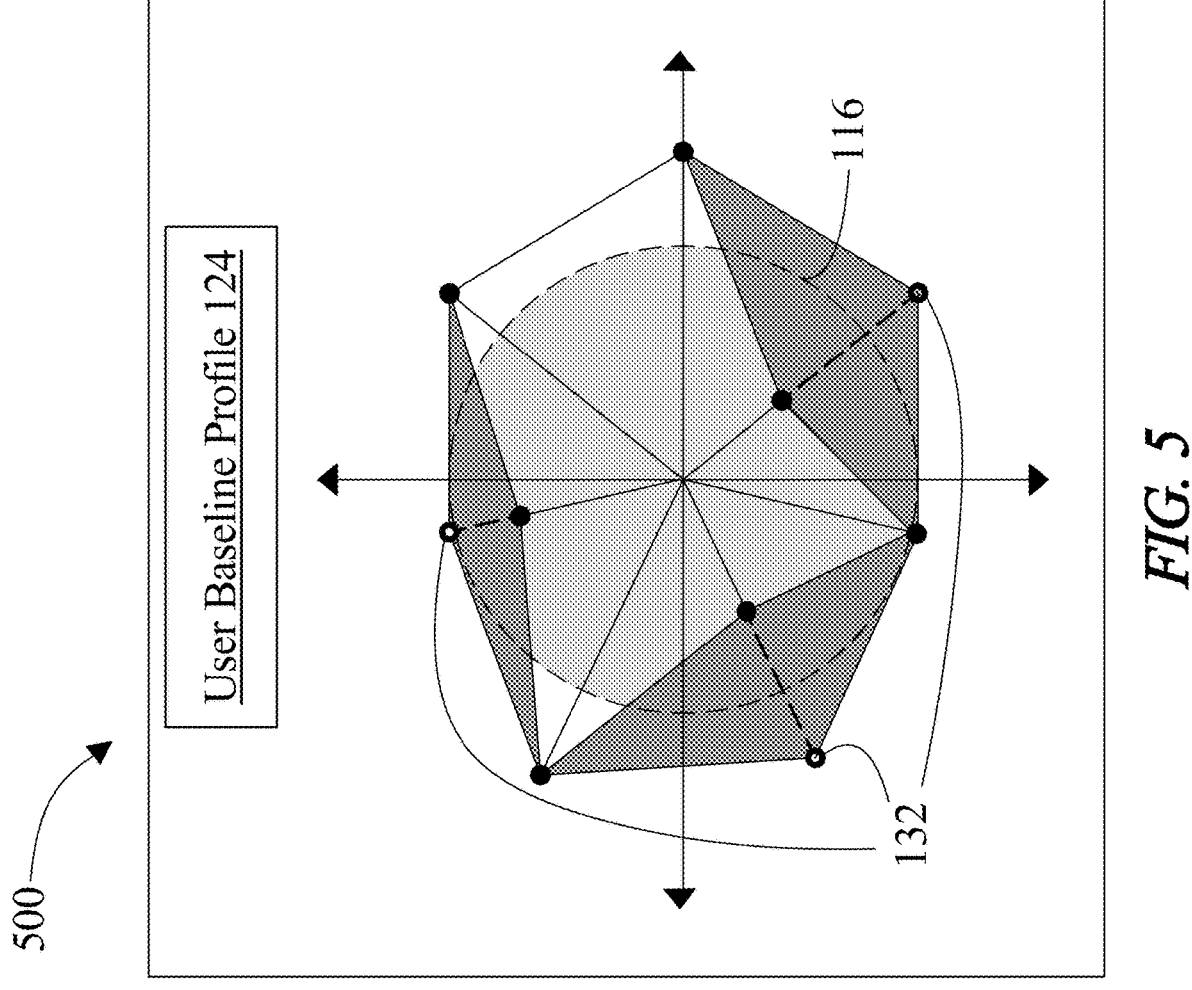
FIG. 5 is a diagrammatic representation of the effect of a plurality of differential actions as a function of a user baseline profile.

Continuing in reference to FIG. 1, weighting a ranked-score list of candidate actions may include using first optimization process 140 to generate a prioritized differential action set 144. First optimization process 140, as described above, may accept an input of a list of candidate differential actions 132 and apply at least a scoring function, or the like, to weight each differential action 132 according to one or more criterion. First optimization process 140 may then rank the candidate set of differential actions 132 into a logical order, for instance and without limitation, a chronological order, a numerically increasing and/or decreasing order, an order based on ease of adoption, etc., based upon the scoring criteria and/or weighting process. First optimization process 140 may then output a prioritized differential action set 144 according to a ranked-score list of actions as they address a physiological goal 116. For instance in non-limiting examples, an first optimization process 140 may input a list of candidate differential actions 132 for addressing a physiological goal 116 of 'improving user body composition within 6 months', and weight the candidate actions based on how easily a user may adopt each differential action 132 based on current user baseline profile 124; the first optimization process 140 may then rank these candidate actions, for instance and without limitation, from easiest to adopt to most difficult to perform to output a ranked-score list of candidate actions that a user may more realistically adhere to accomplish the goal within the 6 month Referring now to FIG. 5, a non-limiting exemplary embodiment of a diagrammatic representation of the effect of a plurality of differential actions as a function of a user baseline profile 500 is illustrated. In non-limiting illustrative embodiments, differential actions 132 denoted as black radial, dashed lines and empty circles, may be applied to a user baseline profile 124 to determine progress toward reaching the physiological goal 116 (dashed circle). Completion of a plurality of differential actions 132 may increase the distance of each black radial, dashed-lines to an empty circle, corresponding to calculated values, functions, vectors, and the like that contain measured data as to the magnitude, degree, timing, and/or impact that each differential action 132 may have in changing the user baseline profile 124 towards achieving a physiological goal 116. A machine-learning process may then calculate the new difference between the shaded region once a plurality of differential actions 132 are completed to the region necessary to achieve a physiological goal 116.

Continuing in reference to FIG. 1, computing device 104 may receive a plurality of user preference data 148. User preference data 148 may be input via a user client device 200. User preference data 148 may be prompted after differential actions 132 have been provided to a user and/or weighting of differential actions 132 may be performed as a function of user preference data 148 provided prior to outputting the prioritized differential action set 144. In non-limiting illustrative examples, user preference data 148 may include selecting which differential actions a user prefers, financial considerations, time constraints, user performance difficulty, geolocation data relating to a user resource availability such as to fitness centers, libraries, pools, clinics, grocery stores, and the like, for performing a differential action 132, among other user preference data. User preference data may be used an input data stored and/or retrieved from a user database 200 by a machine-learning process and/or optimization algorithm generating, measuring, weighting, or otherwise outputting a differential action 132.

Figure 6:
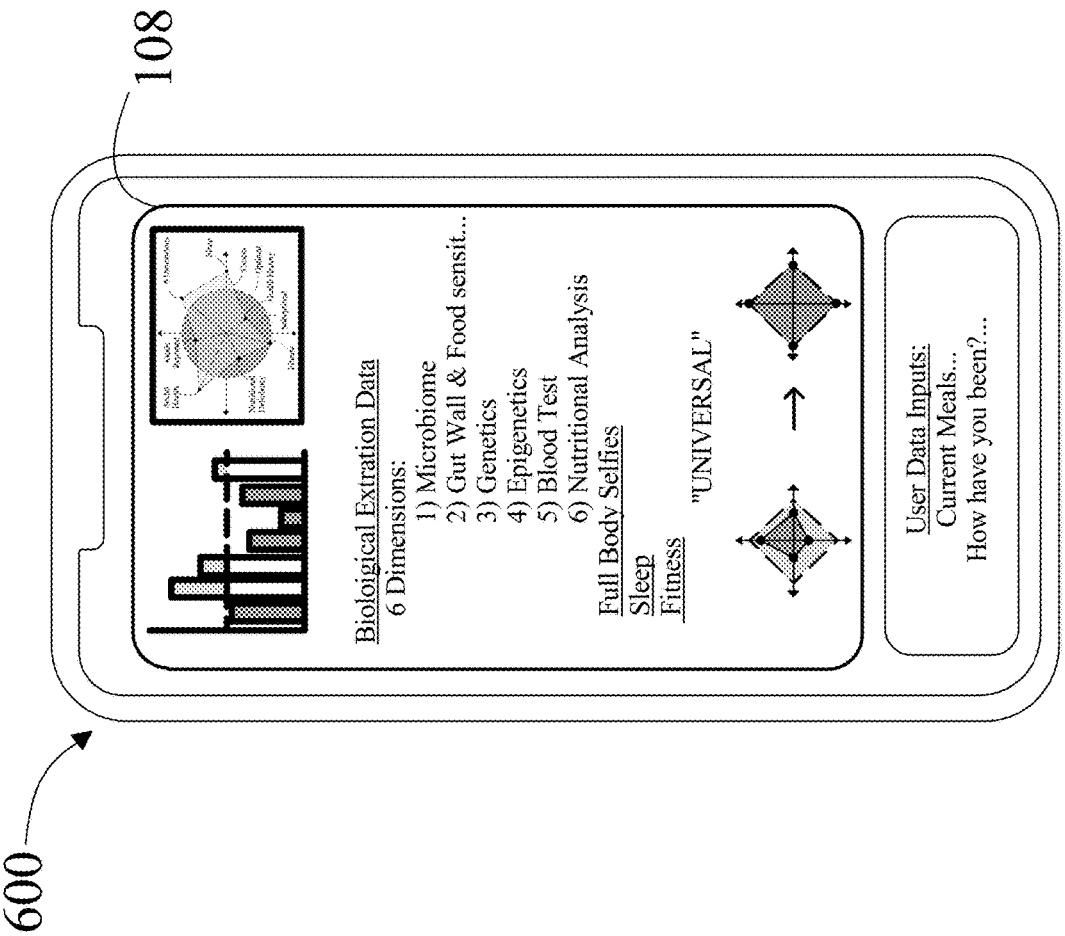
FIG. 6 is a diagrammatic representation of an exemplary embodiment of a user device for providing biological extraction data corresponding to a user

Referring now to FIG. 6, an exemplary embodiment of a user client device 600 for receiving and/or providing a plurality of biological extraction data 108 is illustrated. A computing device 104 may receive and/or provide a plurality of biological extraction data 108 corresponding to the user via a user client device 600, as described in further detail below. Computing device may communicate with a client device, as described in further detail below. User device 600 may display graphical representations of biological extraction data 108, as described in further detail below. User device 600 may provide biological extraction data 108 to via a graphical user interface (GUI), or the like. Persons skilled in the art, upon reviewing the entirety of this disclosure, will be aware of various ways in which graphical displays of biological extraction data 108 may be communicated via a user device 600 to user.

Referring again to FIG. 1, computing device 104 may generate differential action by selecting the differential action 132 from plurality of candidate differential actions 132 as a function of user preference data 148 and at least a physiological goal 116. Selection of differential action 132 may be performed by creating an objective function and then optimizing a selection procedure of an objective function using user preference data 148, physiological goal 116, and/or user baseline profile 124, as previously described. The objective function and/or optimization thereof may be implemented as described above. Alternatively or additionally, selection of a differential action 132 from a plurality of candidate differential actions 132 may be performed by a machine-learning process, as described above.

Continuing in reference to FIG. 1, a computing device 104 may be configured to receive an updated biological extraction datum corresponding to the user, wherein updated biological extraction data 152 may include at least a second element of user data that is more recent in time than a first set of a plurality of biological extraction data 108. "may correspond to a user as an update to any element of biological extraction data 108 after adopting at least a differential action 132. Alternatively or additionally, updated biological extraction data may be new biological extraction data 108 that is of a different category than the first biological extraction data 108 used with a physiological goal 116, as described above.

Continuing in reference to FIG. 1, computing device 104 may use updated biological extraction data 152 to generate an updated user baseline profile 156 using a third machine-learning process 160. Third machine-learning process may be implemented in any manner suitable for implementation of first machine-learning process 112. In an embodiment, third machine-learning process 160 may be the same as a first machine-learning process 112. Third machine-learning process 160 may accept an input of at least an element of updated biological extraction data 152 and a first user baseline profile 124 to generate an output of an updated user baseline profile 156, wherein the updated user baseline profile 156 reflects any changes in biological extraction data 108, as described above. Updated user baseline profile 156 may include changes that reflect a user performing at least a differential action 132, changes that indicate a physiological goal 116 was achieved, and/or changes resulting from a new diagnosis, diet, fitness, sleep, physiological change, or the like. In non-limiting illustrative examples, an updated user baseline profile 156 may reflect changes in a user after beginning a new medication, treatment regimen, or the like, wherein the updated user baseline profile 156 indicates that the user may be eligible for new differential actions 132 and/or physiological goals 116.

Referring now to FIG. 6, an exemplary embodiment of a diagrammatic representation of a plurality of differential actions as a function of a user baseline profile 600 is illustrated. In non-limiting illustrative embodiments, an updated user baseline profile 156 after a user performed a plurality of differential actions 132 may be represented as the original user baseline profile 124, with an increase or decrease in parameters (dark grey shaded area) corresponding to a physiological goal 116 (area within dashed circle). In further non-limiting illustrative embodiments, an updated user baseline profile 156 may be represented by the dark-grey shaded area in addition to the original lighter grey area.

Continuing in reference to FIG. 1, a computing device 104 may modify a differential action 132 as a function of the updated biological extraction data 156 using a fourth machine-learning process 164 and at least a more recent element of user data 152. A fourth machine-learning process 164 may be implemented in any manner suitable for implementation of a first machine-learning process 112. The fourth machine-learning process 164 may accept an input of at least a first differential action 132 and/or a plurality of differential actions 132 and an updated user baseline profile 156 to generate an output of at least an updated differential action 168 as a function of any changes from the updated biological extraction data 152. In non-limiting illustrative examples, an updated differential action 168 may describe a new course of action that resulted from completion, redundancy, and/or elimination of an earlier differential action 132 due to any changes in biological extraction data 108 and/or user preference data 148 reflected in the updated user baseline profile 156. An updated differential action 168 may include a course of action for a user in achieving a first physiological goal 116, a new physiological goal 116, and/or may supplant, be identical to, or be different than a previous differential action 132.

Continuing in reference to FIG. 1, computing device 104 may modify differential action 132 by weighting a new ranked-score list of candidate actions as a function of a physiological goal 116 and the updated user baseline profile 156. A second optimization process 172 may be used to weight at least an updated differential action 168 using a scoring function, and place a plurality updated differential actions 164 into a ranked-score list in a logical order. A second optimization process 172 may be implemented like a first optimization process 140. A logical order may be a chronological ordering, an ascending and/or descending order by step in achieving a desired outcome, an order based upon health impact, severity, or the like, as previously described with a first optimization process 140. A second optimization process 172 may be the same as a first optimization process 140. The second optimization process 172 may weight a list of updated differential actions 164 and/or a first differential action 132, as described above with a first optimization process 140, resulting in an updated ranked-score list of candidate actions 176.

Referring back to FIG. 1, computing device 104 may generate a new prioritized differential action set 180 by calculating an anticipated level of difficulty in achieving a goal for user. Anticipated level of difficulty of an action of an updated ranked-score list of candidate actions 176 may be represented by a numerical value, function, vector, coordinates, or the like, for instance and without limitation, that functions as a signifier matching at least an action and/or an updated differential action 168 to an anticipated level of difficulty. Anticipated level of difficulty may be a signifier that is a quantitative and/or qualitative determination stored and/or retrieved from a database, such as a user database 300, by a machine-learning process and/or optimization process. Alternatively or additionally anticipated level of difficulty may be determined from a variety of factors, for instance and without limitation, tractability of a goal, nature of a goal, number of differential actions that can be found to address the goal, and relative ability of a user to perform differential action, and the like, that is calculated by a machine-learning process. The anticipated level of difficulty may be used as a factor for ranking, scoring, and/or otherwise optimizing a list, ranking, or the like, by an optimization process for generating a list of actions. In non-limiting illustrative examples, a fifth machine-learning process may determine an anticipated level of difficulty of a differential action 132 after an optimization process has generated an updated ranked-score list of candidate actions 176 to output a new prioritized differential action set 180. Alternatively or additionally, in non-limiting illustrative examples, a fourth machine-learning process 164 may determine an anticipated level of difficulty for a differential action by determining how a user performed a first differential action 132, for instance and without limitation, the degree to which a differential action was performed and/or the time of completion prior to a second optimization process 172. In further non-limiting examples, a fourth machine-learning process 164 may retrieve from a database a metric that describes the anticipated level of difficulty for a differential action to be performed in accordance to a user baseline profile, for instance indicating age, surgeries, major hospitalizations, diagnoses, underlying medical conditions, and the like. Although these are physiological considerations associated with a user baseline profile, there are non-physiological elements of data that may be used for calculating the anticipated level of difficulty, for instance and without limitation, user preference data, and geolocated resource availability, and the like. Anticipated level of difficulty may be used as a metric, score, weight, or the like, by a second optimization process 172 to output a new prioritized differential action set 180.

Still referring to FIG. 4, computing device 104 may classify tendencies, deficiencies, preferences, and other data related to the user into impact categories. An "impact category," as used herein, is a classification of data in relation to the impact the information has on a user achieving a goal. Impact categories may include a positive, neutral of negative impact. For example, a positive impact may be tendencies or propensities of the user that help a user achieve their goal. A neutral impact may have no significant effect on a user's progress. A negative impact may refer to a vice or negative propensities/tendencies of the user that decreases a user's progress in achieving their goals. For example, a user's tendency for overtraining may be classified as a negative impact. Computing device 104 may use an impact classifier/machine-learning model configured to receive tendencies, deficiencies, preferences, and other data related to the user as inputs and output impact categories. The training data set may include data correlating inputs as described above to a plurality of impact categories. The impact categories may be displayed through user baseline profile 124.

Referring back to FIG. 1, in response to a negative impact classification, a plurality of differential actions 132 may be generated to deter or correct a user from such tendencies using methods as described above. For example, second machine-learning process 136 may use a training data set specific a negative impact category and negative tendency in prescribing actions to a user to work towards achieving a physiological goal 116. For example, the training data may include data correlating negative tendencies to solutions, corrective measures, resources, and the like. A plurality of specific impact category training data sets for the purposes of generating differential actions 132 may be received from user database 300 as function of the impact classification. Differential actions 132 may include resources or recommendations of different behavioral interventions that can aid a user in eliminating vices" and negative propensities. For example, differential action 132 may be instructions, recommendations, or resources offered to the user such as prescribing the user to join coaching or support group platforms/mediums. These coaching and support platforms may include a coach or a cohort of users sharing similar data as described throughout this disclosure, such as elements of a baseline profile.

Still referring to FIG. 1, computing device 104 may match a user to a coach or a cohort of users who have experienced, are experiencing, have solved, or are trained to help solve the same or a similar negative tendencies to the user for communication, coaching, and/or support, purposes. For example, differential action 132 may include the contact information of a life coach specialized in food therapy for a user to engage with, wherein such information may be received from user database 200, user database 300, and/or another other source or information retrieval method as described throughout this disclosure. Computing device 104 may match a user to a different user (coach) or a cohort of users using a cohort classifier configured to receive negative impacts/negative tendencies, user preference data 128, and the like as inputs and output a match between a user and a different user or a cohort of users. The training data may include data correlating negative impacts and other data related to the user as described above to a plurality of different users such as coaches and members of support groups.

With continued reference to FIG. 1, apparatus 100 may facilitate communication between a user and one or more users. For example, computing device 104 may receive a message, such as audio, text, or graphic based information from a user of the cohorts and display the message for user interaction through a graphical user interface as described above. The user matched to the user of cohorts may be able to respond through the graphical user interface and user device. Messages may include external recourses, such videos, online reading material, digital applications, and the like. The external resources may be digitally attached, for example by a URL, or contained within the message. Communications may include a message from one user to a plurality of user, such as a mass text, email, and the like.

Still referring to FIG. 1, in response to a negative impact classification, computing device 104 may send an electronic notification or alert as part of tracking the user's progress with achieving a goal when a negative tendency is detected. An "alert," as used herein, is a notification configured to draw a user's attention. An alert may be generated as an electronic communication such a text message, email, visual data, audio message and the like. An alert may be transmitted to a computing device operated by the user of through a GUI as described above. An alert may include information identifying a negative tendency, the impact the tendency has on the user's progress, the quantity of times the tendency has been detected/occurred, and the like. For example, computing device 104 may receive updated biological extraction data 152 and other data related to the user or tendency through the user device, on a continuous basis, that is used in generating updated user baseline profile 156 and send an alert when a classified negative tendency, such as overeating, is detected to user for acknowledgement and accountability purposes. The alert may additionally be sent when a user's progress is falling behind. The alert may additionally be sent as reminders for a user to perform their differential actions 132 such as contacting their life coach or engaging in the support group. A "life coach," as used herein, is a professional who works with individuals to help them achieve their personal and professional goals, improve their overall well-being, and make positive changes in their lives. A "support group," as used herein, is a gathering of one or more individuals who come together to share common experiences, challenges, or concerns and provide emotional, practical, and informational support to one another. Computing device 104 may use the alerts to track a user progress, as in if no data is received that the user engages in the prescribed action to fix a negative tendency, such as ignoring the alerts, computing device 104 may recommend additional coaching or support group resources. For example, computing device may use an alert threshold in determining a user's progress in reaching a goal. An "alert threshold," as used herein, is boundary that defines when additional resources need to be generated for user. Additional resources may include updating or replacing the matched life coach, support group, and like. For example, computing device 104 may recommend a second life coach that specifically deals with coaching individuals dealing with the specific reoccurring tendency of the user. The alert threshold may be a numerical value based on frequency of occurrence and duration of patterns, such as, if the same or similar negative tendency is detected and/or was alerted to a user over 5 times in the span of three months, additional resources may be generated. In some embodiments, training data as described above may be updated or trailered to address frequency and/or duration of the specific tendency based on the alert threshold.

Still referring to FIG. 1, in response to a negative impact classification regarding nutrition or nutrient deficiencies, computing device 104 may generate a differential action 132 including an alimentary plan. An "alimentary plan," as used herein, is data reflecting an applicable solution to nourishment requirements, health deficiencies, and other applicable factors associated with the health, nutrition, and wellness of a user. A alimentary plan may include a plurality of food, supplements, beverages, and the like that would correct a nutrient deficiency in a user or aid a user in achieving their physiological goal 116. Computing device 104 may use a nourishment classifier/machine-learning model configured to receive data such elements of user baseline profile, biological extraction, user preferences, physiological goal, and the like as inputs an output a an alimentary plan. The training data set may include data correlating a plurality of inputs as described above to a plurality of foods, supplements, beverages, and the like configured to address the negative impact. Training data may be received from an alimentary database. An "alimentary database," as used herein, is a data structure storing information related to nourishment, nutrients, and wellness, through foods, beverages, supplements, and the like. In some embodiments, computing device 104 may generate an alimentary plan configured to increase or speed up a user's progress. For example, computing device 104 may rank the alimentary classifier outputs using optimization methods a described above to determine optimal foods that would accelerate a user's goal of lowering cholesterol levels.

Still referring to FIG. 1, computing device 104 may reward a user when they achieve a goal or milestone ahead of schedule. Rewards may include an alert/notification notifying a user of accomplishments, highlighting positive trends gained/maintained, negative trends broken/corrected, and the like that illustrates significant efforts the user made to reach their goal. A reward may include mindset training to enhance or continue the progress made. For example, the alert may include a "mindful message," reminding the user to stay on track or with what the overall or bigger picture goal is.

Still referring to FIG. 1, in response to a user accomplishing a physiological goal 116, computing device 104 may link the accomplished goal to a larger vision of optimal health and longevity. The concept of "optimal health and longevity," as used herein, is related to achieving and maintaining the highest possible level of physical, mental, and emotional well-being while promoting a longer and healthier lifespan. For example, optimal health and longevity may include achieving and/or maintaining a balanced diet, regular physical activity, adequate sleep, stress management, avoiding harmful habits, mental stimulation, maintaining social connection, and the like. In other words, computing device 104 may link an accomplished goal to a category, step, or concept related to optimal health and longevity, such as linking a personal diet goal the larger vision of achieving an optimally balanced diet. In some embodiments, computing device 104 may prompt the user through GUI to submit data indicating other goals a user is interested in achieving that ties into the larger vision or overall goal. Computing device 104 may us any optimization process and/or machine-learning process as described above to rank the new goals in most efficient contribution to achieving optimal health and longevity. In some embodiments, computing device 104 may receive user based selection of priority/optimization in accomplishing goals submitted in order to reach optimal health and longevity.

Figure 7:
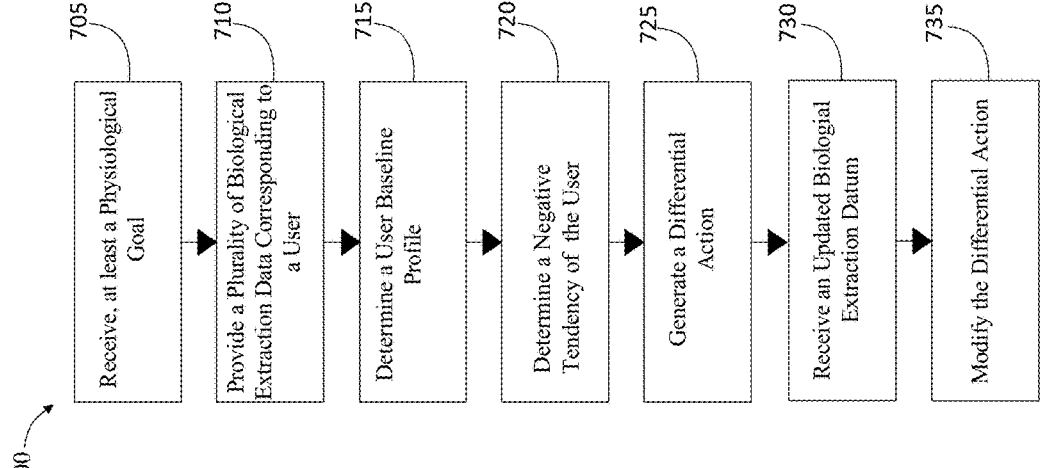
FIG. 7 is a flow diagram illustrating a method of generating rank-ordered instruction sets using an optimization program.

Referring now to FIG. 7, a method of generating rank-ordered instruction sets using an optimization program 700 is illustrated. Method 700 may include using any computing device as described throughout this disclosure. At step 705, method 700 includes receiving from a user, by computing device, at least a physiological goal, for example and with reference to FIGS. 1-6. At step 710, method 700 includes providing, by the computing device, a plurality of biological extraction data corresponding to the user, for example and with reference to FIGS. 1-6. At step 715, method 700 includes determining, by the computing device, a user baseline profile, wherein determining the user baseline profile further includes receiving training data, wherein the training data includes input data and output data, wherein the input data includes biological extraction data elements and physiological goals data elements, and the output data includes user baseline profile data elements; categorizing the training data as a function of a natural language machine learning process, wherein categorizing the training data includes detecting at least one correlation of the biological extraction data elements and the physiological goals data elements with the baseline profile data elements; training a machine-learning model as a function of the categorized training data; and determining, using the trained machine-learning model, the user baseline profile as a function of the plurality of biological extraction data and the at least a physiological goal, for example and with reference to FIGS. 1-6. Determining the user baseline profile may include using a first machine-learning process to determine a correlation between the plurality of biological extraction data corresponding to the user and the at least a physiological goal. At step 720, method 700 includes determining, by the computing device, a negative tendency of the user based on the baseline profile, for example and with reference to FIGS. 1-6. Determining a negative tendency may include classifying a plurality of tendencies of the user to an impact category, wherein the impact category includes a negative impact categorization. The negative impact category may include a user tendency that decreases a user's progress in achieving a physiological goal. Determining the negative tendency may include generating an alert identifying the negative tendency and sending the alert through a graphical user interface.

Still referring to FIG. 7, at step 725, method 700 includes generating, by the computing device, a differential action as a function of the user baseline profile, the negative tendency, and the at least a physiological goal, wherein generating the differential action further includes generating a plurality of candidate differential actions as a function of the user baseline profile and the physiological goal; receiving a plurality of user preference data; and selecting the differential action from the plurality of candidate differential actions as a function of the user preference data and the at least a physiological goal, wherein selecting the differential action includes creating an objective function; and optimizing a selection procedure of the objective function as a function of the user preference data, the at least a physiological goal, the negative tendency, and the user baseline profile, for example and with reference to FIGS. 1-6. The differential action may include coaching resources for the user to correct the negative tendency. The differential action may include support group resources for the user to correct the negative tendency. The differential action may include a alimentary plan configured to solve a nutrient deficiency of the user. At step 730, method 700 includes receiving, by the computing device, an updated biological extraction datum corresponding to the user, for example and with reference to FIGS. 1-6. The he updated biological extraction data may include at least a second element of user data that is more recent in time than the plurality of biological extraction data. Receiving an updated biological extraction datum may include rewarding the user when a goal is achieved. At step 735, method 700 includes modifying, by the computing device, the differential action as a function of the updated biological extraction datum, for example and with reference to FIGS. 1-6.

Figure 8:
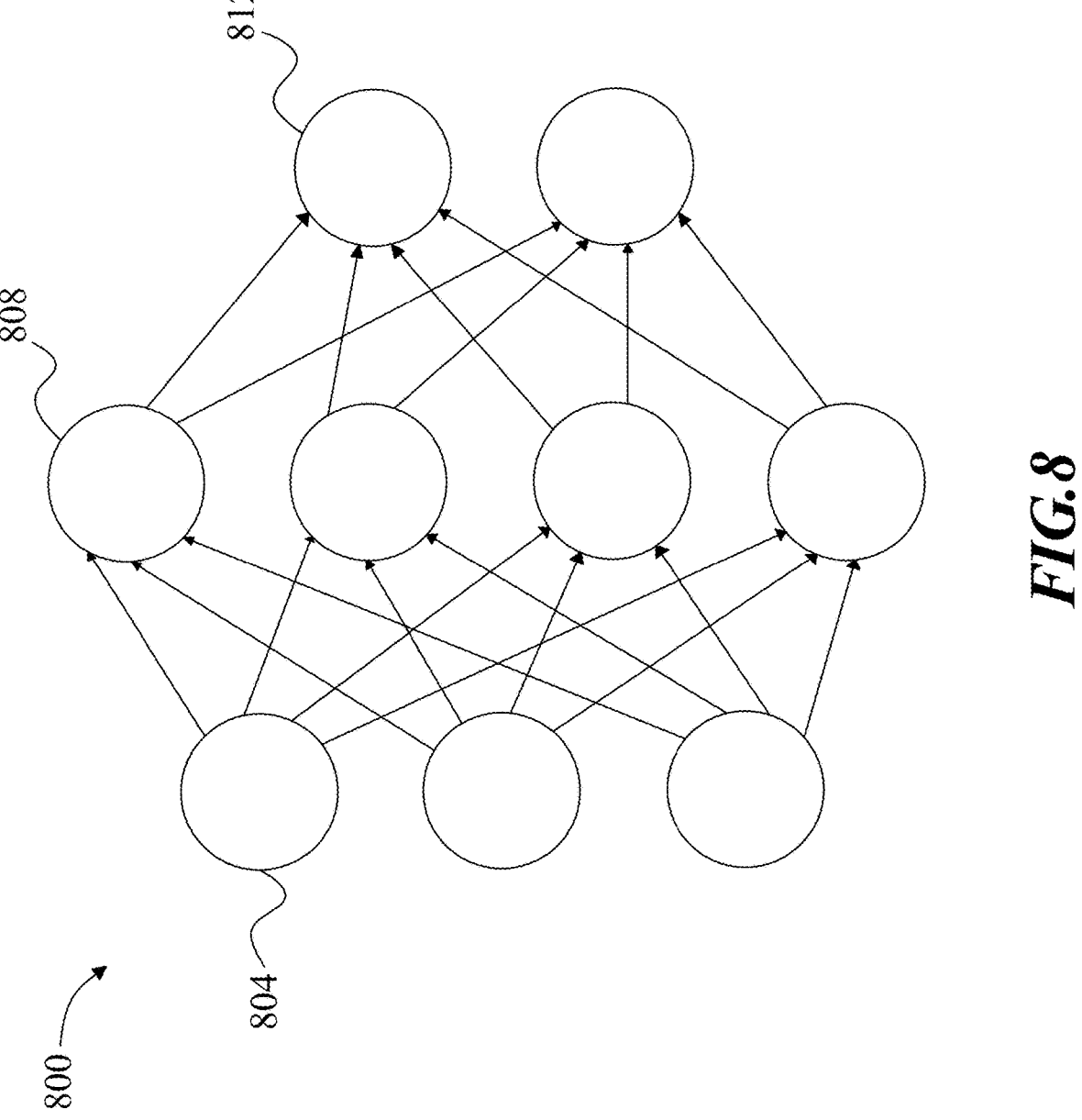
FIG. 8 is a diagram of an exemplary embodiment of neural network.

Referring now to FIG. 8, an exemplary embodiment of neural network 800 is illustrated. A neural network 800 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 804, one or more intermediate layers 808, and an output layer of nodes 812. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 9:
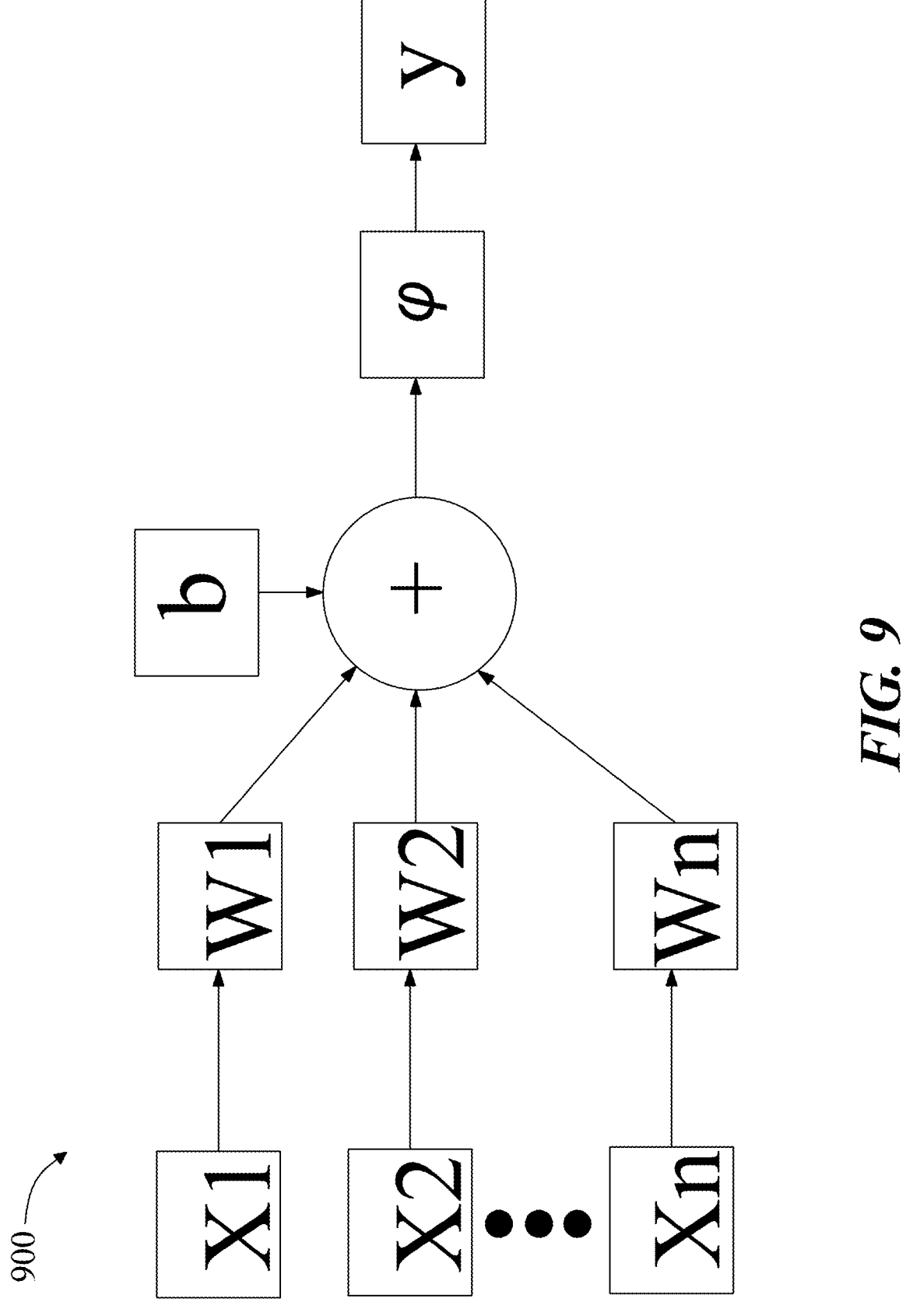
FIG. 9 is a diagram of an exemplary embodiment of a node of a neural network.

Referring now to FIG. 9, an exemplary embodiment of a node 900 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x) = \tanh^2(x)$, a rectified linear unit function such as $f(x) = \max(0,x)$, a "leaky" and/or "parametric" rectified linear unit function such as $f(x) = \max(ax,x)$ for some a, an exponential linear units function such as $$f(x) = \begin{cases} x & \text{for } x \geq 0 \\ \alpha(e^x - 1) & \text{for } x < 0 \end{cases}$$

for some value of $\alpha$ (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x) = x*\text{sigmoid}(x)$, a Gaussian error linear unit function such as $f(x) = a(1 + \tanh(\sqrt{2/\pi}(x + bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function co, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
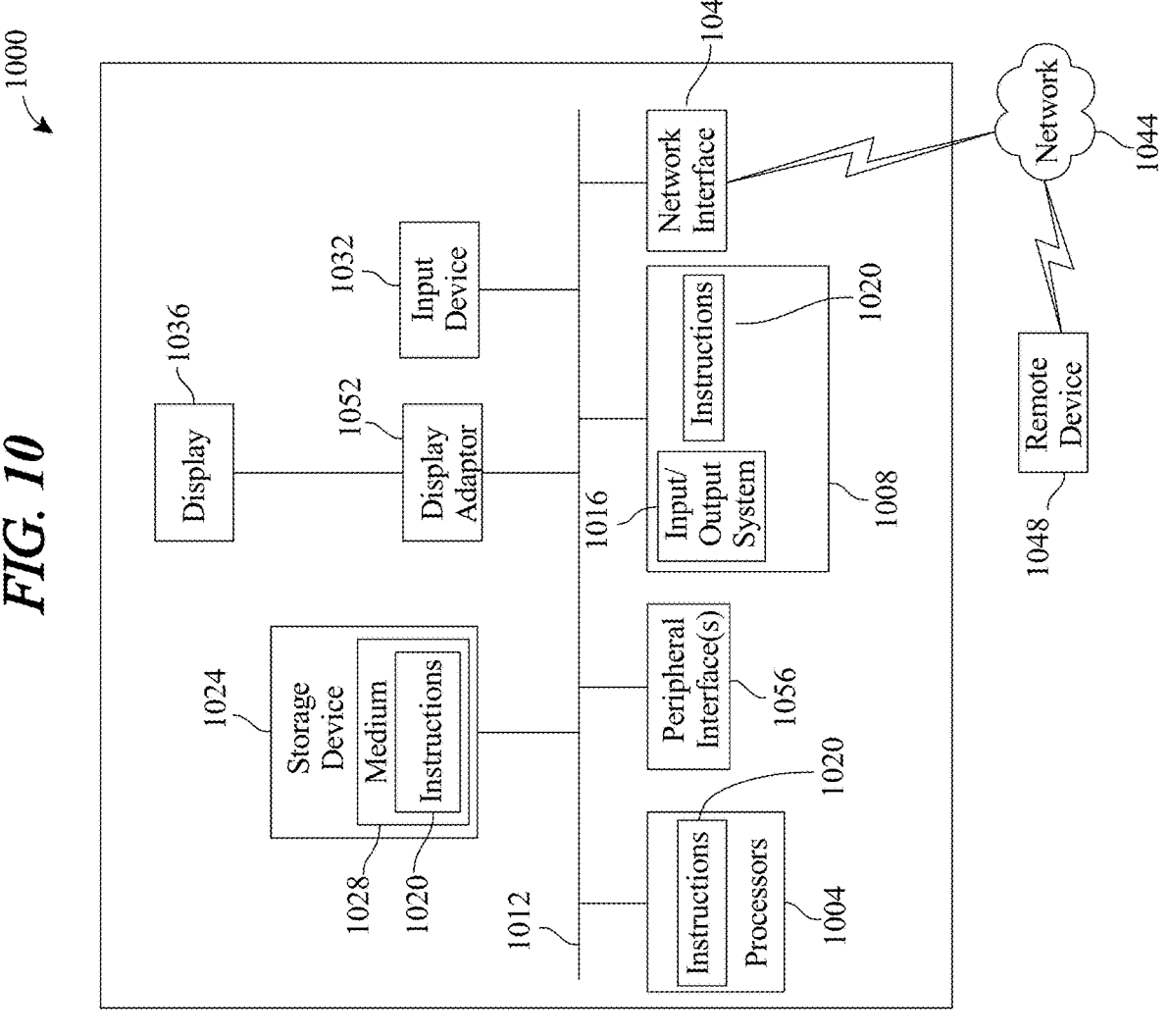
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIRE-WIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for determining a prioritized instruction set for a user, the system comprising a computing device, wherein the computing device is designed and configured to:
   receive, from a user, at least a physiological goal;
   provide a plurality of biological extraction data corresponding to the user;
   determine a user baseline profile, wherein determining the user baseline profile further comprises:
      receiving training data, wherein the training data comprises input data and output data, wherein the input data comprises biological extraction data elements and physiological goals data elements, and the output data comprises user baseline profile data elements;
      categorizing the training data as a function of a natural language machine learning process, wherein categorizing the training data comprises detecting at least one correlation of the biological extraction data elements and the physiological goals data elements with the baseline profile data elements;
      training a machine-learning model as a function of the categorized training data; and
      determining, using the trained machine-learning model, the user baseline profile as a function of the plurality of biological extraction data and the at least a physiological goal;
   determine a negative tendency of the user based on the baseline profile;
   generate a differential action as a function of the user baseline profile, the negative tendency, and the at least a physiological goal, wherein generating the differential action further comprises:
      generating a plurality of candidate differential actions as a function of the user baseline profile and the physiological goal;
      receiving a plurality of user preference data; and
      selecting the differential action from the plurality of candidate differential actions as a function of the user preference data and the at least a physiological goal, wherein selecting the differential action comprises:
         creating an objective function; and optimizing a selection procedure of the objective function as a function of the user preference data, the at least a physiological goal, the negative tendency, and the user baseline profile;

receive an updated biological extraction datum corresponding to the user; and modify the differential action as a function of the updated biological extraction datum.

2. The system of claim 1, wherein determining a negative tendency comprises classifying a plurality of tendencies of the user to an impact category, wherein the impact category comprises a negative impact categorization.

3. The system of claim 2, wherein the negative impact category comprises a user tendency that decreases a user's progress in achieving a physiological goal.

4. The system of claim 1, wherein the differential action comprises coaching resources for the user to correct the negative tendency.

5. The system of claim 1, wherein the differential action comprises support group resources for the user to correct the negative tendency.

6. The system of claim 1, wherein determining the negative tendency comprises:

generating an alert identifying the negative tendency; and sending the alert through a graphical user interface.

7. The system of claim 1, wherein the differential action comprises an alimentary plan configured to solve a nutrient deficiency of the user.

8. The system of claim 1, wherein the updated biological extraction data further comprises at least a second element of user data that is more recent in time than the plurality of biological extraction data.

9. The system of claim 1, wherein receiving an updated biological extraction datum comprises rewarding the user when a goal is achieved.

10. The system of claim 1, wherein determining the user baseline profile further comprises using a first machine-learning process to determine a correlation between the plurality of biological extraction data corresponding to the user and the at least a physiological goal.

11. A method for determining a prioritized instruction set for a user, the method comprising a:

receiving from a user, by computing device, at least a physiological goal;

providing, by the computing device, a plurality of biological extraction data corresponding to the user;

determining, by the computing device, a user baseline profile, wherein determining the user baseline profile further comprises:

receiving training data, wherein the training data comprises input data and output data, wherein the input data comprises biological extraction data elements and physiological goals data elements, and the output data comprises user baseline profile data elements;

categorizing the training data as a function of a natural language machine learning process, wherein categorizing the training data comprises detecting at least one correlation of the biological extraction data elements and the physiological goals data elements with the baseline profile data elements;

training a machine-learning model as a function of the categorized training data; and determining, using the trained machine-learning model, the user baseline profile as a function of the plurality of biological extraction data and the at least a physiological goal;

determining, by the computing device, a negative tendency of the user based on the baseline profile;

generating, by the computing device, a differential action as a function of the user baseline profile, the negative tendency, and the at least a physiological goal, wherein generating the differential action further comprises:

generating a plurality of candidate differential actions as a function of the user baseline profile and the physiological goal;

receiving a plurality of user preference data; and selecting the differential action from the plurality of candidate differential actions as a function of the user preference data and the at least a physiological goal, wherein selecting the differential action comprises:

creating an objective function; and optimizing a selection procedure of the objective function as a function of the user preference data, the at least a physiological goal, the negative tendency, and the user baseline profile;

receiving, by the computing device, an updated biological extraction datum corresponding to the user; and modifying, by the computing device, the differential action as a function of the updated biological extraction datum.

12. The method of claim 11, wherein determining a negative tendency comprises classifying a plurality of tendencies of the user to an impact category, wherein the impact category comprises a negative impact categorization.

13. The method of claim 12, wherein the negative impact category comprises a user tendency that decreases a user's progress in achieving a physiological goal.

14. The method of claim 11, wherein the differential action comprises coaching resources for the user to correct the negative tendency.

15. The method of claim 11, wherein the differential action comprises support group resources for the user to correct the negative tendency.

16. The method of claim 11, wherein determining the negative tendency comprises:

generating an alert identifying the negative tendency; and sending the alert through a graphical user interface.

17. The method of claim 11, wherein the differential action comprises an alimentary plan configured to solve a nutrient deficiency of the user.

18. The method of claim 11, wherein the updated biological extraction data further comprises at least a second element of user data that is more recent in time than the plurality of biological extraction data.

19. The method of claim 11, wherein receiving an updated biological extraction datum comprises rewarding the user when a goal is achieved.

20. The method of claim 11, wherein determining the user baseline profile further comprises using a first machine-learning process to determine a correlation between the plurality of biological extraction data corresponding to the user and the at least a physiological goal.

* * * * *